US011971181B2

(12) United States Patent
Brown et al.

(10) Patent No.: US 11,971,181 B2
(45) Date of Patent: Apr. 30, 2024

(54) SYSTEM AND METHOD FOR MONITORING AIR QUALITY WHILE COOLING AN OUTDOOR ELECTRONIC DISPLAY ASSEMBLY

(71) Applicant: Precision Systems Integration, LLC, Cumming, GA (US)

(72) Inventors: Mike Brown, Cumming, GA (US); William Dunn, Alpharetta, GA (US); Doug Bennett, Alpharetta, GA (US)

(73) Assignee: Precision Systems Integration, LLC, Cumming, GA (US)

( * ) Notice: Subject to any disclaimer, the term of this patent is extended or adjusted under 35 U.S.C. 154(b) by 0 days.

(21) Appl. No.: 18/368,397

(22) Filed: Sep. 14, 2023

(65) Prior Publication Data

US 2024/0003565 A1    Jan. 4, 2024

Related U.S. Application Data

(63) Continuation of application No. 16/521,337, filed on Jul. 24, 2019, now Pat. No. 11,796,198.
(Continued)

(51) Int. Cl.
*F24F 11/30* (2018.01)
*F24F 11/52* (2018.01)
(Continued)

(52) U.S. Cl.
CPC ............. *F24F 11/30* (2018.01); *F24F 11/52* (2018.01); *F24F 11/74* (2018.01);
(Continued)

(58) Field of Classification Search
CPC ........... G01N 33/0009; G01N 33/0031; G01N 33/0063; G01N 33/0037; G01N 33/0039;
(Continued)

(56) References Cited

U.S. PATENT DOCUMENTS 3,415,178 A    12/1968    Ball et al.
7,389,158 B2    6/2008    Desrochers et al.
(Continued)

FOREIGN PATENT DOCUMENTS

| CN | 104879155 A | 9/2015 |
| CN | 105115049 A | 12/2015 |
| CN | 106765790 A | 5/2017 |

OTHER PUBLICATIONS

United States Environmental Protection Agency, Visualize Trends, webpage, Jul. 16, 2019, 2 pages.
(Continued)

*Primary Examiner* — Benjamin R Schmitt
(74) *Attorney, Agent, or Firm* — Standley Law Group LLP; Jeffrey S. Standley; Adam J. Smith

(57) ABSTRACT

Devices, systems, and method for monitoring air quality are provided. Digital out-of-home advertising display units are located within a geographic area. The units include an electronic display for displaying advertising images located at a housing, an open loop pathway for ambient air extending between an ingestion and exhaustion area of the housing. An air quality monitoring device located along the open loop pathway includes comprising sensor(s) for measuring characteristics of encountered gasses which are electronically communicated by a network connectivity device to a monitoring station. The monitoring station generates visual representations of the received measurements, at least one of which summarizes the measurements from multiple ones of the units.

20 Claims, 6 Drawing Sheets

Related U.S. Application Data

(60) Provisional application No. 62/702,382, filed on Jul. 24, 2018.

(51) Int. Cl.
*F24F 11/74* (2018.01)
*G01N 33/00* (2006.01)
*F24F 11/00* (2018.01)

(52) U.S. Cl.
CPC ..... *G01N 33/0009* (2013.01); *G01N 33/0031* (2013.01); *G01N 33/0063* (2013.01); *F24F 2011/0006* (2013.01); *G01N 33/0037* (2013.01); *G01N 33/0039* (2013.01); *G01N 33/004* (2013.01); *G01N 33/0042* (2013.01); *G01N 33/0044* (2013.01)

(58) Field of Classification Search
CPC ............ G01N 33/004; G01N 33/0042; G01N 33/0044; F24F 11/30; F24F 11/52; F24F 11/74; F24F 2011/0006
See application file for complete search history.

(56) References Cited

U.S. PATENT DOCUMENTS

| | | | |
|---|---|---|---|
| 8,373,841 B2 | 2/2013 | Dunn | |
| 8,472,174 B2 | 6/2013 | Idems et al. | |
| 8,591,455 B2 | 11/2013 | Mensinger et al. | |
| 8,654,302 B2 | 2/2014 | Dunn et al. | |
| 8,767,165 B2 | 7/2014 | Dunn | |
| 8,790,005 B2 | 7/2014 | Tylinski et al. | |
| 8,854,595 B2 | 10/2014 | Dunn | |
| 9,026,310 B2 | 5/2015 | Tran et al. | |
| 9,370,127 B2 | 6/2016 | Dunn | |
| 2003/0163369 A1 | 8/2003 | Arr | |
| 2007/0181000 A1 | 8/2007 | Wilson et al. | |
| 2008/0045156 A1* | 2/2008 | Sakhpara | G01N 33/0063 455/66.1 |
| 2009/0268404 A1* | 10/2009 | Chu | H05K 7/20745 361/698 |
| 2012/0026432 A1 | 2/2012 | Dunn et al. | |
| 2013/0038470 A1 | 2/2013 | Niemeyer et al. | |
| 2015/0224437 A1 | 8/2015 | Nygren | |
| 2015/0330817 A1 | 11/2015 | Law et al. | |
| 2016/0011158 A1 | 1/2016 | Liu et al. | |
| 2017/0023457 A1 | 1/2017 | Hart et al. | |
| 2017/0074453 A1 | 3/2017 | Bowers et al. | |
| 2017/0083043 A1 | 3/2017 | Bowers et al. | |
| 2017/0106218 A1 | 4/2017 | Lin et al. | |
| 2017/0193788 A1 | 7/2017 | Kim et al. | |
| 2017/0284906 A1 | 10/2017 | Xing et al. | |
| 2017/0351221 A1 | 12/2017 | Balti et al. | |
| 2018/0299161 A1 | 10/2018 | Ribbich et al. | |

OTHER PUBLICATIONS

Bradford Zone, Bradford trials air quality monitoring unites from InLink, webpage, Jul. 16, 2019, 2 pages.
Array of Things, Welcome homepage, webpage, Jul. 15, 2019, 10 pages.
Smartcities World News, Uk cities use digital street units to measure air quality, webpage article, Jul. 16, 2019, 2 pages.
Sensors, The Role of Advanced Sensing in Smart Cities, journal article, Dec. 27, 2012, 33 pages.
United States Environmental Protection Agency, Air Sensor Guidebook, Jun. 2014, 73 pages.
Thomas, How Gas Detectors Work, webpage, Jul. 11, 2019, 4 pages.

\* cited by examiner

SYSTEM AND METHOD FOR MONITORING AIR QUALITY WHILE COOLING AN OUTDOOR ELECTRONIC DISPLAY ASSEMBLY

CROSS-REFERENCE TO RELATED APPLICATION

This application is a continuation of U.S. application Ser. No. 16/521,337 filed Jul. 24, 20219, which claims the benefit of U.S. Provisional Patent Application No. 62/702,382 filed Jul. 24, 2018, the disclosures of each of which are hereby incorporated by reference as if fully restated herein.

TECHNICAL FIELD

Exemplary embodiments relate generally to a system and method for monitoring air quality, particularly while cooling an outdoor electronic display assembly.

BACKGROUND AND SUMMARY OF THE INVENTION

More and more individuals are paying attention to the quality of the air they breathe. As such, monitoring air quality has become increasingly important. The increasing awareness of air quality issues is driven, at least in part, by the increase in environmental pollutants that ordinary citizens are exposed to. This increase in environmental pollutants is driven, at least in part, by increasing urbanization. To combat air quality issues, city planners, engineers, scientists, geologists, architects, and the like have begun monitoring and considering air quality issues when planning, constructing, maintaining, studying, and renovating urban landscapes. For example, without limitation, studies are increasingly being perform to analyze how geography and urban landscapes are affecting air quality and the environment. These studies have revealed phenomena like urban heat islands and canyons which exist within cities and can create air quality issues.

Air quality monitors exist which can be used to monitor air quality by measuring the concentration of various pollutants and other compounds in a sample of air as well as various characteristics of the sample of air. However, existing air quality monitors are expensive and cumbersome to use. Additionally, to get useful air quality readings and an accurate depiction of overall air quality, such monitors must be deployed in many locations across a city or other geographic area. Each of these air quality monitors must be powered and protected. The use of just one or two, or even a dozen, individual air quality monitors often does not provide enough data for one to draw reliable conclusions from. Furthermore, the expensive nature of such air quality monitors makes them a desirable target for thieves, vandals, and other criminals. Further still, such air quality monitors are often affixed to structures such as buildings or telephone poles which may need replaced or moved periodically. Even slight movements in location of such sensors can drastically impact the readings, thus making the data unreliable. Therefore, what is needed is a powered and protected air quality monitor that can be placed in a multi-purpose structure.

The present disclosures provide a powered and protected air quality monitor that can be placed in a multi-purpose structure. For example, without limitation, electronic displays are increasingly being used throughout cities for advertisement, messaging, wayfinding, and the like. Such electronic displays are often placed in ruggedized assemblies to protect the various components of the display from the elements, vandalism, and the like. However, the environmental conditions, and sometimes the sealed or semi-sealed nature of the ruggedized assemblies, requires that the assemblies be thermally managed. Such thermal management is often accomplished, at least in part, by ingesting ambient air. The ingested ambient air may be circulated through the assembly and placed in direct or indirect contact with various components of the assembly before being exhausted back into the ambient environment.

Circulation of ambient air through such assemblies provides an opportunity for air quality monitoring. In exemplary embodiments, an air quality monitor is placed within the path of ingested ambient air. The air quality monitor may comprise one or more sensors placed on a board. The board may be placed within a housing. Seals may be placed between the board and the housing to substantially seal the housing.

The sensors may be exposed to the ambient air ingested by the assembly. In exemplary embodiments, the sensors are placed above riser ducts located along intake ductwork such that a portion of the ingested ambient air is sufficiently slowed before contacting the sensors and then traveling on through the remainder of the assembly. The intake ductwork may form a substantially "L" shape and a drain may be located along the horizontal portion of the intake ductwork to drain any ingested moisture.

In other exemplary embodiments, the sensors may be placed within a protective housing. The protective housing may comprise one or more features such as deflectors, walls, baffles, holes, fans, some combination thereof, or the like, which slow the air down sufficiently to permit readings at an air quality sensor. The protective housing may also provide for water protection.

The air quality monitor may be powered by existing power supplies provided by the assembly. The air quality monitor may be otherwise protected by the housing for the air quality monitor as well as the housing for the assembly. This arrangement has the further advantage of not disrupting the aesthetic appearance of the assembly or the surrounding cityscape or geography.

Further features and advantages of the devices and systems disclosed herein, as well as the structure and operation of various aspects of the present disclosure, are described in detail below with reference to the accompanying figures.

BRIEF DESCRIPTION OF THE DRAWINGS

In addition to the features mentioned above, other aspects of the present invention will be readily apparent from the following descriptions of the drawings and exemplary embodiments, wherein like reference numerals across the several views refer to identical or equivalent features, and wherein.

DETAILED DESCRIPTION OF EXEMPLARY EMBODIMENT(S)

Various embodiments of the present invention will now be described in detail with reference to the accompanying drawings. In the following description, specific details such as detailed configuration and components are merely provided to assist the overall understanding of these embodiments of the present invention. Therefore, it should be apparent to those skilled in the art that various changes and modifications of the embodiments described herein can be made without departing from the scope and spirit of the present invention. In addition, descriptions of well-known functions and constructions are omitted for clarity and conciseness.

Embodiments of the invention are described herein with reference to illustrations of idealized embodiments (and intermediate structures) of the invention. As such, variations from the shapes of the illustrations as a result, for example, of manufacturing techniques and/or tolerances, are to be expected. Thus, embodiments of the invention should not be construed as limited to the particular shapes of regions illustrated herein but are to include deviations in shapes that result, for example, from manufacturing.

Figure 1:
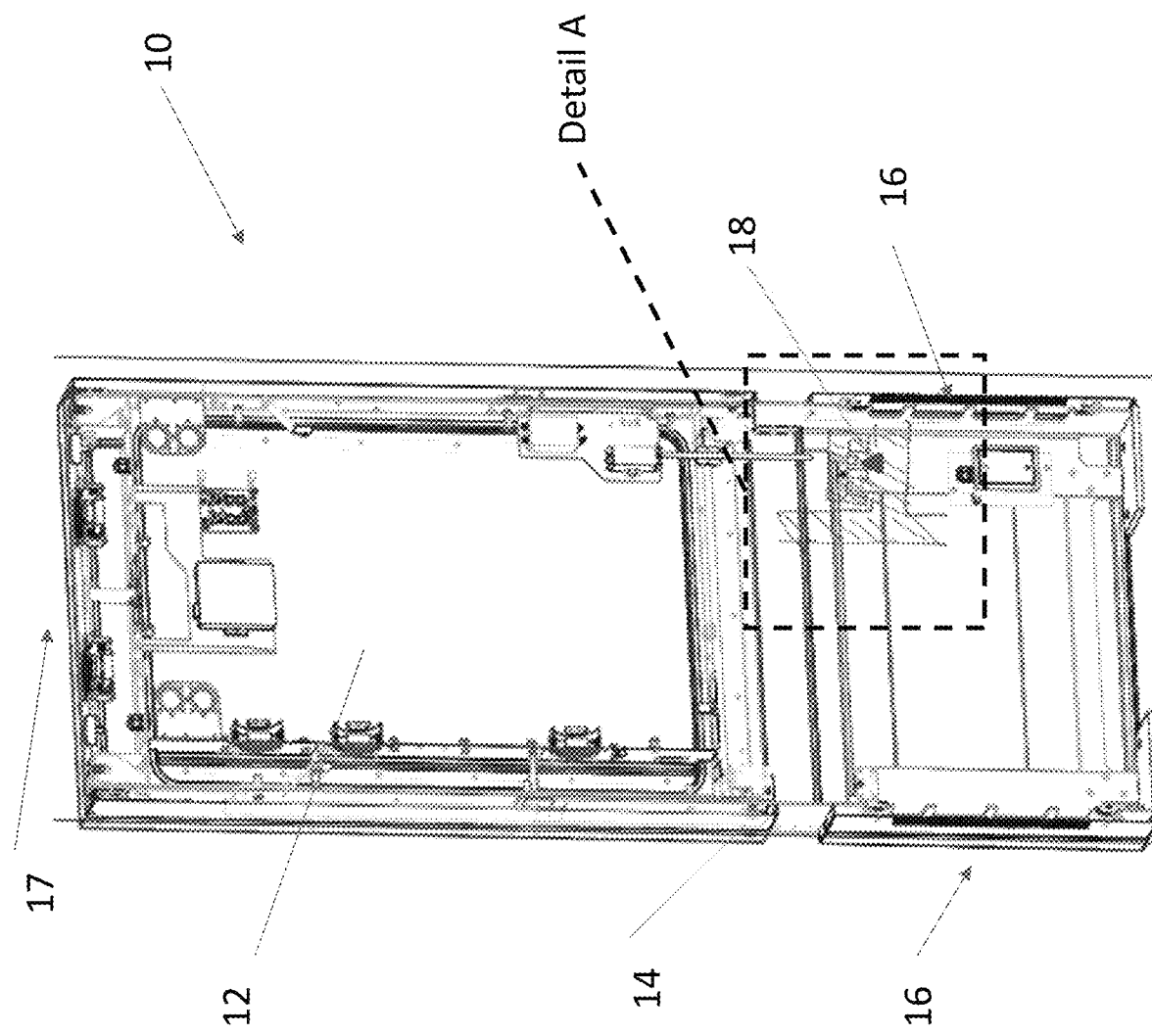
FIG. 1 is a perspective view of an exemplary display assembly also indicating Detail A.

FIG. 1 is a perspective view of an exemplary display assembly 10. The display assembly 10 may comprise a housing 14. The housing 14 may be of any size or shape. In exemplary embodiments, the housing 14 is configured to be mounted or otherwise secured to a sidewalk. In other exemplary embodiments, the housing 14 is configured to be mounted or otherwise secured to the ground, a building, a storefront, a wall, the roof of a vehicle, the side of a bus shelter, or the like. In still other exemplary embodiments, the housing 14 is configured to be placed in a suspended arrangement from a ceiling or other overhead member, such as but not limited to, for placement in a window.

The display assembly 10 may comprise one or more electronic displays 12 located within said housing 14. The electronic displays 12 may be any type of electronic display 12 such as, but not limited to, liquid crystal display, organic light emitting diode, light emitting diode, plasma, cathode ray tube, or the like. The electronic display 12 may comprise a backlight assembly. Backlighting may be provided directly or by edge light. Alternatively, or in addition, the display assembly 10 may be configured to hold one or more illuminated posters. In exemplary embodiments, two electronic display 12 may be positioned in a back to back arrangement on the housing 14, though any number and arrangement of electronic displays 12 is contemplated. The electronic display 12 may be oriented in landscape, portrait, or the like.

The display assembly 10 may comprise a thermal management system. The display assembly 10 may comprise one or more intake areas 16 and one or more exhaust areas 17. In exemplary embodiments, the intake area(s) 16 may be located on the bottom half of the assembly 10 and the exhaust area(s) 17 may be located on the upper half of the assembly, though any location of the intake and exhaust areas 16 and 17 are contemplated.

Ambient air 15 may be ingested through the intake area(s) 16. The ambient air 15 may travel through one or more ducts 18 located within the display assembly 10 and contact various heat generating components such as, but not limited to, the electronic display 12 (including the backlight assembly), power modules, video players, processors, electronic storage devices, network connectivity devices, and other electronic equipment for the electronic display 12 and other components of the assembly 10. Such contact may be direct, or may be indirect, such as but not limited to, by way of convection, conduction, heat exchangers, thermoelectric devices, some combination thereof, or the like. Any number of fans may be located along, adjacent to, or otherwise in gaseous communication with the ducts 18, the intake areas 16, the exhaust areas 17, some combination thereof, or the like to facilitate the ingestion, movement, and/or exhaustion of the ambient air.

The thermal management system may comprise one or more open loop pathways, which may extend through some or all of the housing 10. The open loop pathways may be configured to receive ambient air. The thermal management system may further comprise one or more closed loop pathways, which may extend through some or all of the housing 10. The closed loop pathways may be configured to receive circulating gas. Any number of fans may be located along, adjacent to, or otherwise in gaseous communication with the closed loop pathway to facilitate the ingestion, movement, and/or exhaustion of the ambient air.

The closed loop pathway(s) may be configured to thermally interact with the open loop pathway(s). In exemplary embodiments, the closed loop pathway(s) may be substantially sealed so as to prevent contaminates potentially present in the ambient air from entering the circulating gas. In exemplary embodiments, the closed loop pathway(s) may substantially surround the electronic displays 12. The closed loop may, for example without limitation, pass in front of the electronic display 12 and into an area behind the electronic display, though any location is contemplated. The open loop may, for example without limitation, pass along a rear surface of the backlight assembly for the electronic display, though any location is contemplated. The ambient air 15 may eventually be exhausted from the display assembly 10 by way of the exhaust area(s) 17. In this way the pathway of the ambient air 15 may form an open loop.

Figure 2:
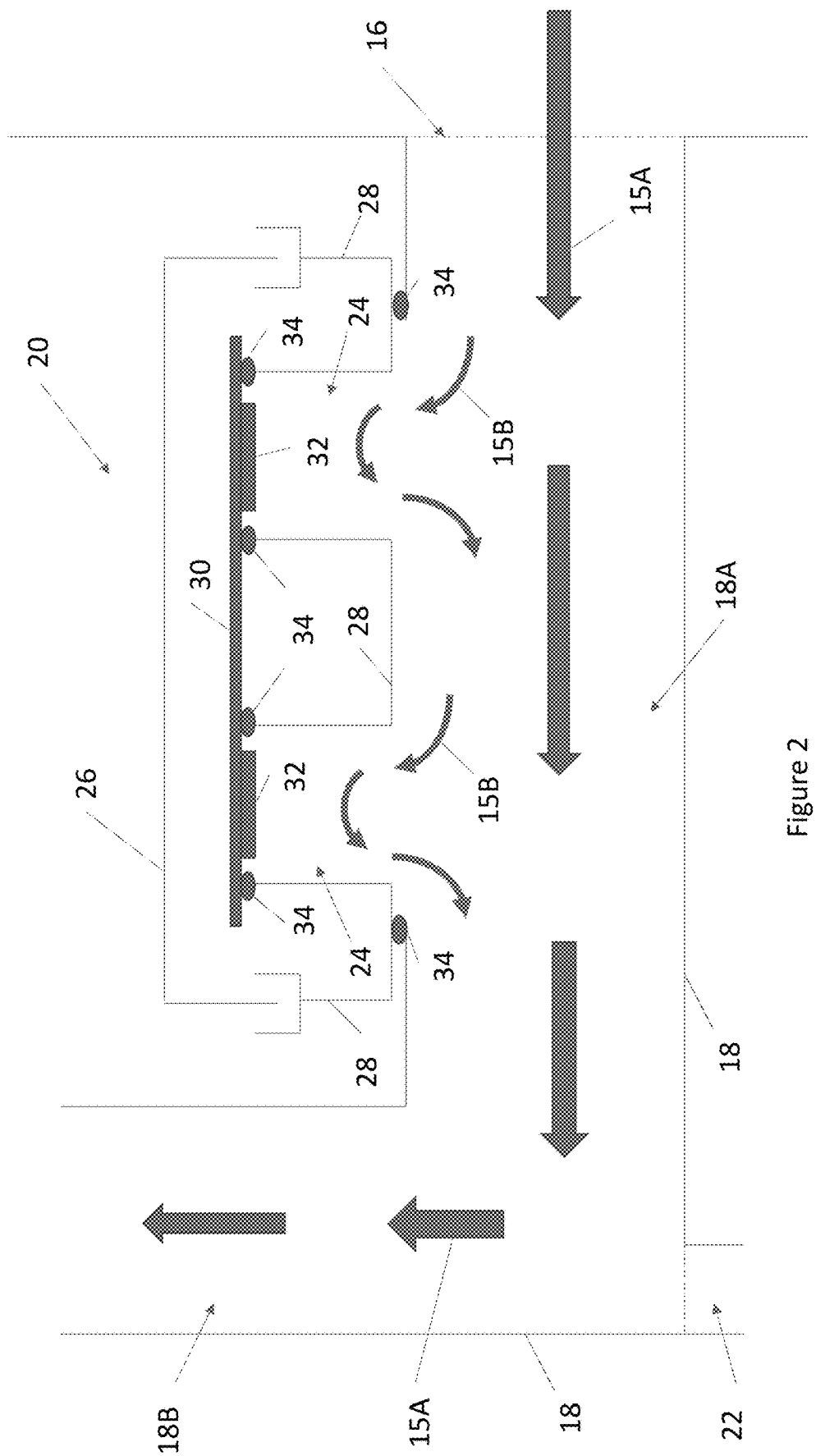
FIG. 2 is a detailed sectional view of Detail A of FIG. 1.

FIG. 2 is a detailed sectional view of Detail A of FIG. 1. An air quality monitoring device 20 may be placed along, adjacent to, or in proximity with the path of at least a portion of the ingested ambient air 15A. In exemplary embodiments, the air quality monitoring device 20 is placed along the ducts 18 such that the air quality monitoring device 20 is in fluid communication with at least a portion of the ingested ambient air 15A. In exemplary embodiments, a first portion of the duct 18A travels substantially horizontally inward from the intake 16 and a second portion of the duct 18B travels substantially vertically upward from the first portion of the duct 18A. However, any shape, size, and arrangement of the ductwork 18 is contemplated such that the ductwork 18 may comprise any number of portions traveling any number of directions.

A drain 22 may be located at one or more locations along the ductwork 18. The drain 22 may be configured to remove moisture or other debris that are contained within the ingested ambient air 15A or are ingested with the ambient air 15A. For example, without limitation, rain, snow, dust, and the like may be ingested with the ambient air 15A and removed by way of the drain 22. In exemplary embodiments, the drain 22 is located along a lower edge of the first portion of the duct 18A, preferably where the first portion of the duct 18A meets the second portion of the duct 18B. Some or all of the ductwork 18 may be angled towards the drains 22.

One or more risers 24 may extend from the duct 18 to various portions of the air quality monitoring device 20. In exemplary embodiments, the risers 24 may extend from an upper edge of the substantially horizontal portion of the duct 18A. The air quality monitoring device 20 may comprise a housing having an upper portion 26 and a lower portion 28, though any number of portions of any size and/or shape are contemplated. The upper portion 26 may be selectively joined with a lower portion 28 in a substantially sealed arrangement. The upper and lower portions 26 and 28 of the housing may at least partially surround an air quality sensor board 30. In exemplary embodiments, the upper portion 26 and the lower portion 28 of the housing are configured to be joined to one another. The upper and lower portions 26 and 28 may join one another in a substantially airtight or watertight fashion. The air quality sensor board 30, in exemplary embodiments, is a printed circuit board.

One or more sensors 32 may be mounted to the air quality sensor board 30. One or more seals 34 may be placed between the sensors 32 and the air quality sensor board 30 and/or the lower housing 28. The sensors 32 may be in electronic communication with the air quality sensor board 30.

The sensors 32 may be configured to take various air quality measurements. The upper and lower housing 26 and 28 may entirely or partially expose some or all of the sensors 32 such that at least a portion of the sensors 32 may remain exposed to at least a portion 15B of the ingested ambient air 15A. In this way, the sensors 32 may be placed in gaseous communication with at least a representative portion 15B of the ingested ambient air 15A. In exemplary embodiments, such gaseous communication is made by way of the risers 24, though such is not required. The risers 24 may slow the portion of the ingested ambient air 15 contacting the sensors 32 in order to provide a more accurate reading. Additionally, the risers 24 may ensure that little to no moisture ingested with the ambient air 15 contacts the sensors 32.

Figure 3:
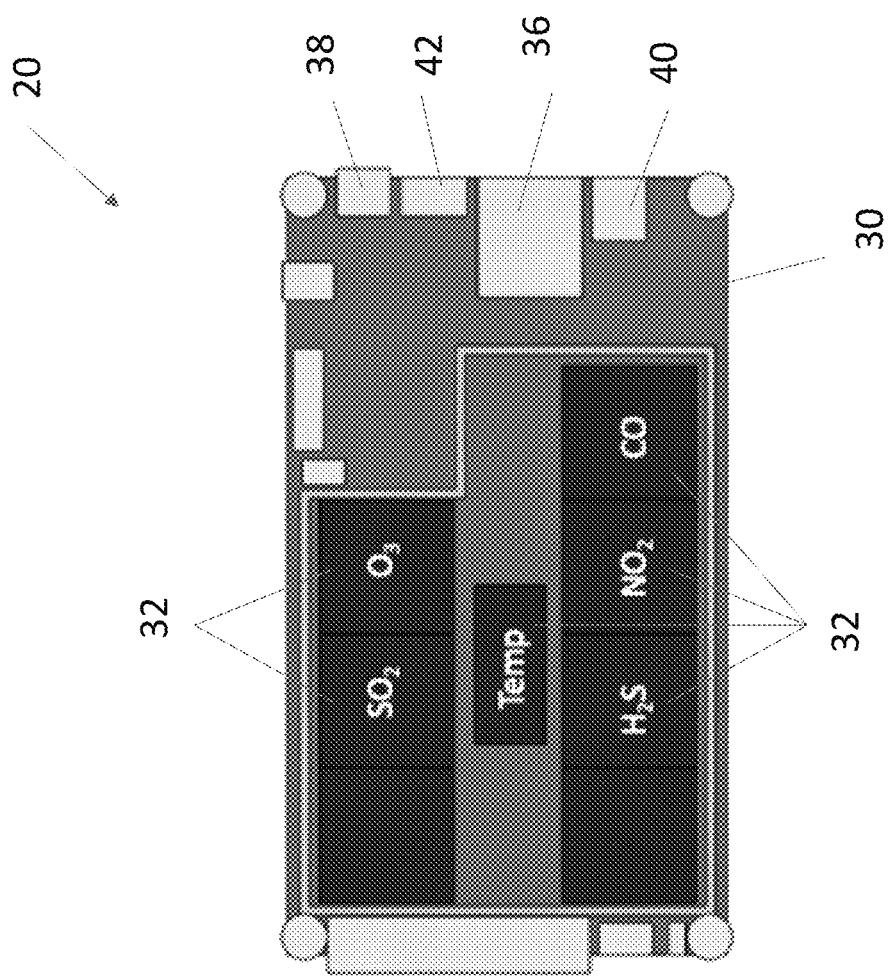
FIG. 3 is a plan view of an exemplary air quality monitoring device.

FIG. 3 is a plan view of an exemplary air quality monitoring device 20 for use with the display assembly 10. The sensors 32 may be configured to measure the concentrations of various gas pollutants. The gas pollutants may be those defined by the Environmental Protection Agency (EPA), though such is not required. The sensors 32 may be configured to measure one or more of: particulate, pollution, pollen, ambient temperature, humidity, air pressure, or the like. In exemplary embodiments, the sensors 32 may be configured to measure the concentration of one or more of compounds such as, but not limited to: carbon dioxide, nitrogen dioxide, ozone, trioxygen, sulfur dioxide, hydrogen sulfide, carbon monoxide, some combination thereof, or the like. The sensors 32 may be further configured to measure one or more characteristics of the ingested ambient air 15 such as, but not limited to: temperature, humidity, pressure, air speed, some combination thereof, or the like. One or more sensors 32 may be provided to measure one or more of the compounds and/or characteristics. Alternatively, or additionally, each of the sensors 32 may comprise one or more cells each configured to measure one or more particular compounds and/or characteristics. It is contemplated that the sensors 32 may be configured to measure any type or number of compounds and/or characteristics of the ambient air 15. In exemplary embodiments, temperature and/or other measurements may be taken over a geographic area and/or period of time in order to determine the existence, size, shape, and the like of various phenomena such as, but not limited to, urban heat islands and canyons.

In exemplary embodiments, the sensors 32 may be configured to detect the presences and/or concentration of particular chemicals and/or compounds, such as but not limited to, those found in explosives, chemical weapons, biological weapons, nuclear weapons, some combination thereof or the like. Alternatively, or additionally, the sensors 32 may be configured to detect the presence of radioactive materials in the air, such as but not limited, to the presences and/or concentration of certain isotopes.

The air quality sensor board 30 may comprise one or more components such as, but not limited to: power module(s) 36, electronic storage device(s) 38, processor(s) 40, network connectivity device(s) 42, some combination thereof, or the like. In other exemplary embodiments, the air quality monitoring device 20 may not comprise such components. The air quality monitoring device 20 may be in electrical connection with one or more components such as, but not limited to: a power module(s) 36, electronic storage device(s) 38, processor(s) 40, network connectivity device(s) 42, some combination thereof, or the like. The air quality monitoring device 20 may be in communication with any number of components provided in the assembly 10 to support the electronic display 12, related components, and other components of the assembly 10. This arrangement may reduce the cost and complexity of manufacturing and installing such air quality monitors 20.

Figure 4:
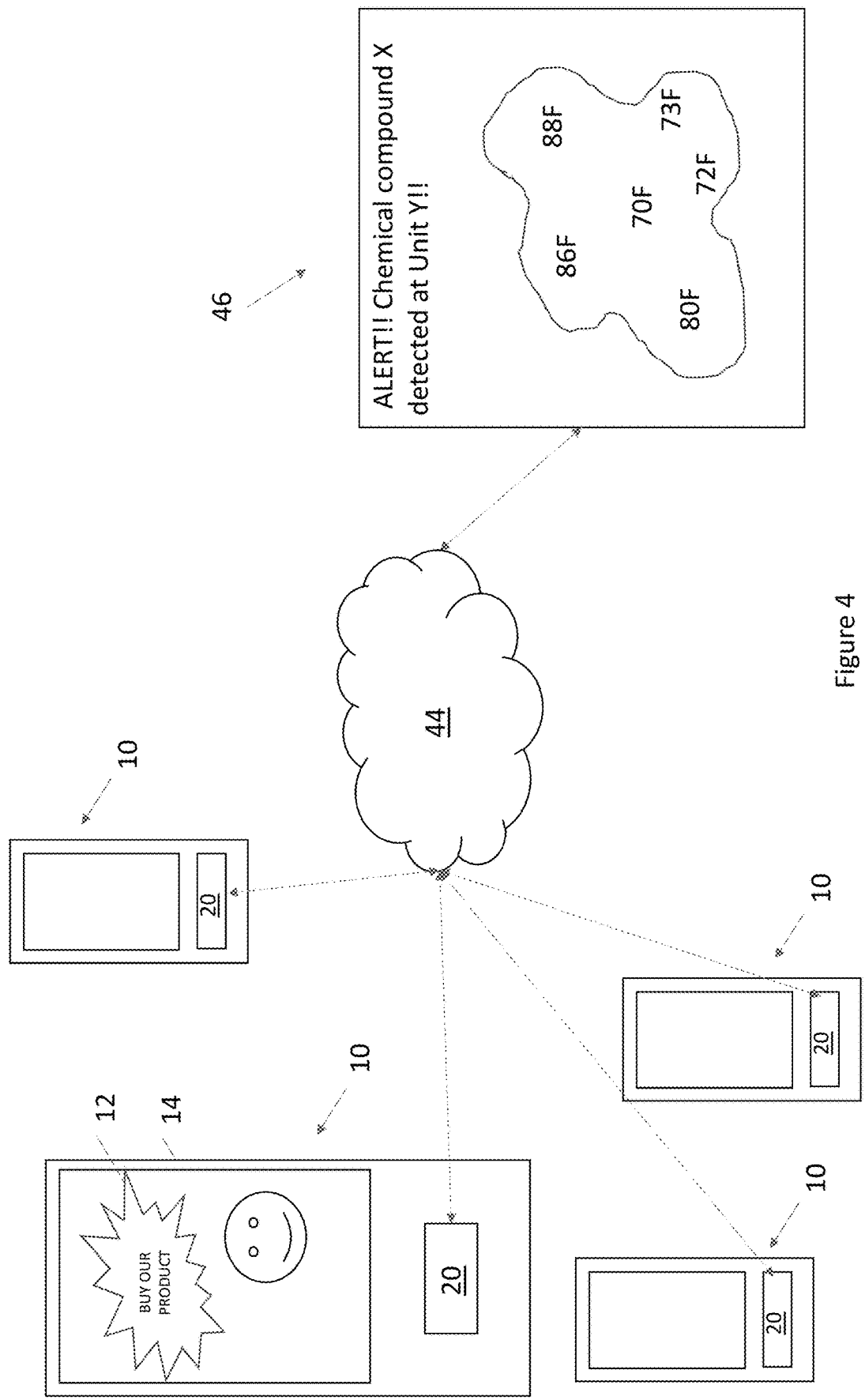
FIG. 4 is a simplified block diagram of an exemplary system.

FIG. 4 is a simplified block diagram of an exemplary system for use with the display assembly 10. As a number of such display assemblies 10 may be deployed throughout a city or other geographic area, the integration of such air quality monitors 20 with the display assemblies 10 may provide a convenient system and method for monitoring air quality in a city or geographic area. In particular, the air quality monitors may be powered and networked for electronic communication with one or more monitoring stations 46 by way of air quality sensor board 30 and/or the existing electronic components in the assemblies 10. Additionally, the air quality monitoring device 20 may be otherwise protected by the existing housing 12 for the assembly 10. This may also reduce the cost and complexity of manufacturing and installing such air quality monitors 20. This has the further advantage of not disrupting the aesthetic appearance of the assembly 10 or the surrounding cityscape or geography. Furthermore, the use of ambient air otherwise provided from the open loop may provide more accurate sampling of the surrounding environment, particularly as compared to natural convection. Natural convection may be more affected by localized conditions and may result in re-ingestion. Forced airflow may take sample from further away and may be less affected by localized conditions resulting in more accurate measurements.

The monitoring stations 46, in exemplary embodiments without limitation, may be configured to generate a visual representation of the city or other geographic area overlaid with the measurements from the various display assemblies 10. The monitoring stations 46 may be further configured to display the alerts. The monitoring stations 46 may be configured to display other visual representations of the measurements such as, but not limited to, listings, charts, graphs, tables, some combination thereof, and the like.

In exemplary embodiments, one of more of the electronic storage device(s) 38, processor(s) 40, network connectivity device(s) 42 may be in electrical connection with the power module(s) 36. One or more of the electronic storage device(s) 38, the processor(s) 40, and the network connectivity device(s) 42 may alternatively be in electronic communication with one another. The network connectivity device(s) 42 may be in communication with one or more monitoring stations 46 by way of a network 44. The network 44 may be the internet, intranet, cellular network, the world wide web, or the like. The monitoring stations 46 may be a physical center and/or one or more electronic devices computers, tablets, smartphones, a database, a server, a monitoring center, a command center, some combination thereof, or the like.

The processor 40 may continuously and/or periodically direct the sensor 32 to take one or more measurements from the sensor 32. The processor 40 may so direct the sensor 32 to take such measurements at any frequency or interval. The measurements taken by the sensors 32 may be interpreted by the processor(s) 40. The measurements taken by the sensors 32 may be stored as air quality data on electronic storage device(s) 38. The air quality data may be transmitted to one or more monitoring stations 46 by way of the network connectivity device(s) 42. Instructions for operation of the air quality monitoring device 20 may be periodically transmitted to the various display assemblies 10 from the monitoring stations 46. For example, without limitation, the frequency, interval, types, and the like of measurements taken may be altered. As additional examples, without limitation, thresholds, types, and the like of alerts may be altered. Instructions may be stored on the electronic storage device 38 and executed by the processor 40. The processors 40 may be configured to automatically generate an alert when chemicals, compounds, or other components of the ingested ambient air 15B are detected and/or found to be within a certain range, outside a certain rage, above a certain threshold, below a certain threshold, some combination thereof, or the like.

Figure 5B:
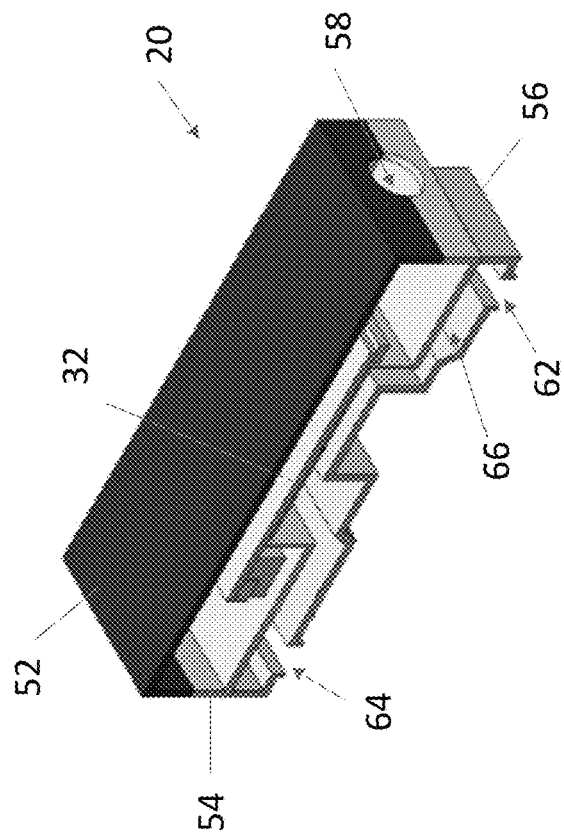
FIG. 5B is a perspective sectional view of the air quality monitoring device of FIG. 5A.
Figure 5A:
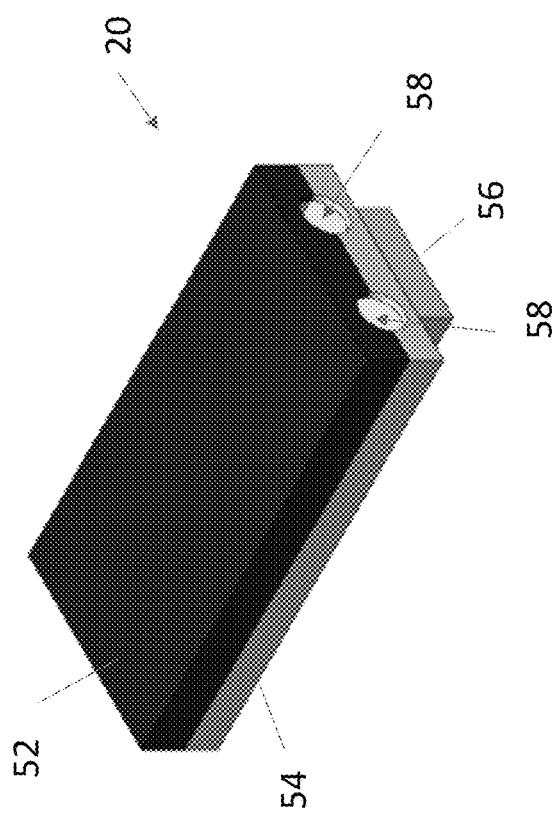
FIG. 5A is a perspective view of another exemplary embodiment of the air quality monitoring device.

FIG. 5A is a perspective view of another exemplary embodiment of the air quality monitoring device 20. The air quality monitoring device 20 may comprise a first housing portion 52, a second housing portion 54, and a third housing portion 56, though any number, size, shape, configuration, and type of housing portions are contemplated. One or more apertures 58 may be provided for access to the sensors 32 stored within. For example, without limitation, the apertures 58 may provide access for servicing, power connectivity, network connectivity, or the like.

FIG. 5B is a perspective sectional view of the air quality monitoring device 20. The second housing portion 54 may be configured to support the sensors 32 and/or the air quality sensor board 30. Alternatively, or additionally, other portions of the housing 52 and 56 may be used to support the sensors 32 and/or the air quality sensor board 30. An entrance aperture 62 may be provided within the third housing portion 56. An exit aperture 64 may be provided within the third housing portion 56. Alternatively, or additionally, it is contemplated that the entrance aperture 62 and/or the exit aperture 64 may be provided in other portions of the housing 52 and 56. Furthermore, it is contemplated that the exit aperture 64 may be used for the ingestion of ambient air 15B into the air quality monitoring device 20 and that the entrance aperture 62 may be used for the exhaustion of ambient air 15B from the air quality monitoring device.

An air pathway 66 may extend between the entrance aperture 62 and the exit aperture 64. The air pathway 66 may extend through some or all of the air quality monitoring device 20. The airflow pathway 66 may be configured to slow the speed of the flow of ambient air 15B passing through the air quality monitoring device 20. For example, without limitation, one or more structural features and/or modifications, such as but not limited to, risers, baffles, walls, ramped surfaces, holes, channels, sloped surfaces, textured surfaces, some combination thereof, or the like, may be provided along some or all of the airflow pathway 66. The airflow pathway 66 may be configured to provide a desirable flow rate, pressure, speed, amount, some combination thereof, or the like, of the portion of the ambient air 15B which travels through the air quality monitoring device 20.

In exemplary embodiments, the sensors 32 may be mounted above the air pathway 66. The sensors 32 may be oriented in a downward facing position towards the ground such that the sensor's 32 exposure to any moisture and/or contaminants in the ambient air 15B may be minimized. In exemplary embodiments, one or more fans may be mounted within, along, or in proximity to the air quality monitoring device 20 so as to force a portion 15B of the ingested ambient air 15A into the air quality monitoring device 20.

Figure 6:
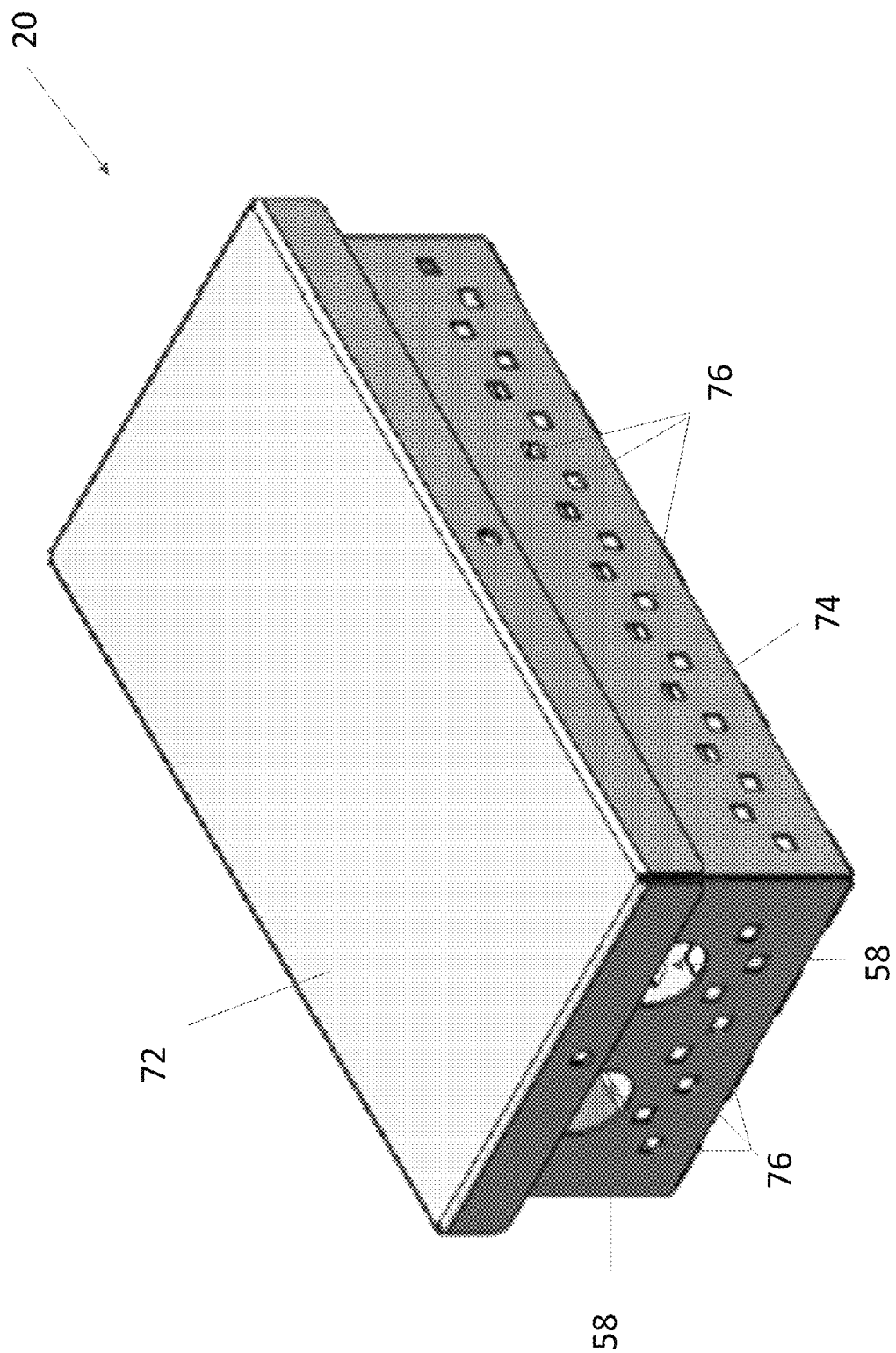
FIG. 6 is a perspective view of another exemplary embodiment of the air quality monitoring device.

FIG. 6 is a perspective view of another exemplary embodiment of the air quality monitoring device 20. The air quality monitoring device 20 may comprise a housing. A lower portion 74 of the housing may be generally shaped as a cuboid with an open upper surface. An upper portion 72 of the housing may be sized to cover at least the open upper surface defined by the lower portion 74. The upper portion 72 may serve as a lid. A number of apertures 76 may be located on one or more surfaces of the lower portion 74. Alternatively, or additionally, the apertures 76 may be located on one or more surfaces of the upper portion 72. The size, shape, location, and/or number of apertures 76 may be selected to control the amount, flow rate, pressure, speed, some combination thereof, or the like, of the ambient air 15A is gathered to form the portion 15B which travels through the air quality monitoring device 20. One or more apertures 58 may be provided for access to the sensors 32 stored within.

The air quality monitoring device 20, and/or various components thereof, may be comprised of stainless steel, though any material is contemplated.

Any embodiment of the present invention may include any of the optional or preferred features of the other embodiments of the present invention. The exemplary embodiments herein disclosed are not intended to be exhaustive or to unnecessarily limit the scope of the invention. The exemplary embodiments were chosen and described in order to explain the principles of the present invention so that others skilled in the art may practice the invention. Having shown and described exemplary embodiments of the present invention, those skilled in the art will realize that many variations and modifications may be made to the described invention. Many of those variations and modifications will provide the same result and fall within the spirit of the claimed invention. It is the intention, therefore, to limit the invention only as indicated by the scope of the claims.

Certain operations described herein may be performed by one or more electronic devices. Each electronic device may comprise one or more processors, electronic storage devices, executable software instructions, and the like configured to perform the operations described herein. The electronic devices may be general purpose computers or specialized computing device. The electronic devices may be personal computers, smartphone, tablets, databases, servers, or the like. The electronic connections described herein may be accomplished by wired or wireless means.

What is claimed is:

1. A system for monitoring air quality of a geographic area, said system comprising:
digital out-of-home advertising display units, each provided at a respective, fixed location within the geographic area and comprising:
an electronic display for displaying advertising images;
a housing for said electronic display, said housing having an ingestion area and an exhaustion area;

an open loop pathway for ambient air extending between said ingestion area and said exhaustion area;

an air quality monitoring device located along said open loop pathway and comprising one or more sensors for measuring characteristics of encountered gases; and a network connectivity device in electronic communication with the air quality monitoring device; and a monitoring station in electronic communication with each of the digital out-of-home advertising display units, wherein said monitoring station is configured to:

receive measurements from said one or more sensors of said air quality monitoring devices of each of said digital out-of-home advertising display units by way of the network connectivity devices; and generate visual representations of said measurements from said digital out-of-home advertising display units, including a first visual representation summarizing said measurements of multiple ones of said digital out-of-home advertising display units and a second visual representation of multiple ones of said measurements of a given one of said digital out-of-home advertising display units over a period of time.

2. The system of claim 1 wherein:
said electronic display is located at a forward-facing side of said housing and covers at least a majority of said forward-facing side.

3. The system of claim 2 wherein:
each of said digital out-of-home advertising display units comprises a common power supply for at least the air quality monitoring device and the electronic display.

4. The system of claim 1 wherein:
the one or more sensors are located at an upper surface of a housing of said air quality monitoring device and each are oriented to face toward a ground surface.

5. The system of claim 4 wherein:
the housing of said air quality monitoring device comprises apertures which permit a portion of the ambient air in the open loop pathway to interact with each of said one or more sensors.

6. The system of claim 1 wherein:
said first visual representation comprises a map of the geographic area with the measurements displayed at areas of the map corresponding with locations of the digital out-of-home advertising display units.

7. The system of claim 6 wherein:
the characteristics comprise air temperatures.

8. The system of claim 6 wherein:
the characteristics comprise concentrations of various gases.

9. The system of claim 6 wherein:
the characteristics comprise air temperatures and concentrations of at least one of: sulfur dioxide, trioxygen, hydrogen sulfide, nitrogen dioxide, and carbon monoxide.

10. The system of claim 1 wherein:
the characteristics comprise concentrations of various gases; and
the monitoring station is configured to generate an alert where the concentration of any of the various gases exceed a respective, predetermined threshold.

11. The system of claim 10 wherein:
the various gases comprise sulfur dioxide, trioxygen, hydrogen sulfide, nitrogen dioxide, and carbon monoxide.

12. The system of claim 10 wherein:
the monitoring station is configured to transmit the alert to at least one remote electronic device.

13. The system of claim 1 wherein:
each of said digital out-of-home advertising display units comprise at least one additional airflow pathway separated from the airflow pathway.

14. The system of claim 13 wherein:
said at least one additional airflow pathway comprises a closed loop pathway for circulating gas fluidly separated from said airflow pathway.

15. The system of claim 1 wherein:
said electronic display comprises a directly backlit electronic display.

16. A method for monitoring air quality of a geographic area, said method comprising:
providing digital out-of-home advertising display units, each provided at a respective, fixed location within the geographic area and comprising:
an electronic display for displaying advertising images;
a housing for said electronic display, said housing having an ingestion area and an exhaustion area;
an open loop pathway for ambient air extending between said ingestion area and said exhaustion area;
an air quality monitoring device located along said open loop pathway and comprising one or more sensors for measuring characteristics of encountered gases; and
a network connectivity device in electronic communication with the air quality monitoring device;
receiving, at a monitoring station in electronic communication with each of the digital out-of-home advertising display units, measurements from said one or more sensors of said air quality monitoring devices of each of said digital out-of-home advertising display units by way of the network connectivity devices; and
generating visual representations of said measurements from said digital out-of-home advertising display units, including a first visual representation summarizing said measurements of multiple ones of said digital out-of-home advertising display units and a second visual representation of multiple of said measurements of a given one of said digital out-of-home advertising display units over a period of time.

17. The method of claim 16 wherein:
said at least one visual representation comprises a map of the geographic area with the measurements displayed at areas of the map corresponding with locations of the digital out-of-home advertising display units; and
the characteristics comprise air temperatures and concentrations of at least one of: sulfur dioxide, trioxygen, hydrogen sulfide, nitrogen dioxide, and carbon monoxide.

18. The method of claim 17 wherein:
each of said digital out-of-home advertising display units comprises a closed loop pathway for circulating gas fluidly separated from said airflow pathway;
said electronic display of each of said digital out-of-home advertising display units comprises a directly backlit electronic display;
the one or more sensors are located at an upper surface of a housing of said air quality monitoring device and each are oriented to face toward a ground surface; and
the housing of said air quality monitoring device comprises apertures which permit a portion of the ambient air in the open loop pathway to interact with each of said one or more sensors.

19. The method of claim 16 further comprising:
generating, at the monitoring station, an alert where the concentration of any of the various gases exceed a respective, predetermined threshold; and
electronically transmitting, by way of the monitoring station, the alert to at least one remote electronic device.

20. A system for monitoring air quality trends for a geographic area, said system comprising:
digital out-of-home advertising display units, each provided at a respective, fixed location within the geographic area and comprising:
an electronic display for displaying advertising images;
a housing for said electronic display, said housing having an ingestion area and an exhaustion area;
an open loop pathway for ambient air extending between said ingestion area and said exhaustion area;
an air quality monitoring device located along said open loop pathway and comprising one or more sensors for measuring characteristics of encountered gases; and
a network connectivity device in electronic communication with the air quality monitoring device; and
a monitoring station in electronic communication with each of the digital out-of-home advertising display units, wherein said monitoring station is configured to:
receive and store measurements from said one or more sensors of each of said air quality monitoring devices of each of said digital out-of-home advertising display units by way of the network connectivity devices over a period of time; and
generate at least one summarization of said measurements of multiple ones of said digital out-of-home advertising display units and at least one data output of said measurements of a given one of said digital out-of-home advertising display units over a period of time.

\* \* \* \* \*